United States Patent [19]

Lee et al.

[11] Patent Number: 4,873,377

[45] Date of Patent: Oct. 10, 1989

[54] PREPARATION OF DIBROMONEOPENTYL GLYCOL

[75] Inventors: John Y. Lee; Edgar E. Spielman, Jr., both of Baton Rouge, La.

[73] Assignee: Ethyl Corporation, Richmond, Va.

[21] Appl. No.: 251,787

[22] Filed: Oct. 3, 1988

[51] Int. Cl.⁴ ............................................. C07C 31/42
[52] U.S. Cl. .................................................... 568/844
[58] Field of Search ......................................... 568/844

[56] References Cited

U.S. PATENT DOCUMENTS

| | | | |
|---|---|---|---|
| 3,876,509 | 4/1975 | Davis et al. | 568/844 |
| 3,883,581 | 5/1975 | Davis et al. | 568/844 |
| 3,932,541 | 1/1976 | Davis et al. | 568/844 |
| 4,154,966 | 5/1979 | Weil | 568/844 |

*Primary Examiner*—Howard T. Mars
*Attorney, Agent, or Firm*—E. E. Spielman, Jr.

[57] ABSTRACT

This invention relates to a process for preparing DBNPG by brominating pentaerythritol with HBr in the presence of a catalyst and solvent wherein water is present during the process. The reaction mass is neutralized prior to recovery of the DBNPG from the reaction mass.

10 Claims, No Drawings

PREPARATION OF DIBROMONEOPENTYL GLYCOL

BACKGROUND OF THE INVENTION

This invention relates to a process for producing dibromoneopentyl glycol.

Dibromoneopentyl glycol (DBNPG) is a commercial, reactive fire retardant having especially useful qualities in polyester- and polyurethane-based formulations.

DBNPG is generally prepared by reacting pentaerythritol with HBr in the presence of a catalyst and a reaction solvent. To assure enhanced acceptability in the market, the DBNPG product obtained should be very pure. Particularly troublesome impurities are monobromopentaerythritol and tribromoneopentyl alcohol.

It is therefore an object of this invention to provide a process for preparing a very pure DBNPG product.

THE INVENTION

The process of this invention comprises brominating pentaerythritol with HBr to yield a reaction mass containing dibromoneopentyl glycol and lesser amounts of monobromopentaerythritol and tribromoneopentyl alcohol. The bromination occurs in the presence of a catalyst selected from the group consisting of mono- or di-carboxylic acids, their anhydrides, their esters, and mixtures thereof, and in the presence of a substantially inert solvent. The solvent has a solubility for the tribromoneopentyl alcohol greater than that for the dibromoneopentyl glycol at the temperature to which the reaction mass will be cooled later in the process to effect the formation of a precipitate which is predominant in dibromoneopentyl glycol. During the process of this invention, at least a major portion of the by-product water formed by the bromination is maintained in the reaction mass. After the bromination is complete, the reaction mass is neutralized and then cooled sufficiently to form the precipitate which is predominant in dibromoneopentyl glycol. The precipitate is then recovered from the reaction mass.

The total amount of HBr fed to the reactor containing the pentaerythritol provides a molar ratio of pentaerythritol to HBr of at least 1:2. Preferably this molar ratio is within the range of from about 1:2.5 to about 1:3.0. The excess of HBr provided by the preferred range insures the predominant formation of DBNPG over the formation of the mono- and tri-bromo species. Molar ratios much in excess of 1:3 are not desirable as the DBNPG yield will be decreased while the yield of tribromoneopentyl alcohol will be increased. Also, some of the excess HBr will be absorbed by the water present in the reaction mass so that the water present will have an HBr content of at least 50 wt %. Maintenance of at least a 50 wt % HBr concentration in the water is important so that the water cannot hydrolyze the brominated products to form undesirable polymers and other by-products.

The HBr can be fed to the reactor as gaseous HBr or as aqueous HBr. Gaseous HBr is preferred. In both cases the HBr is preferably added at a rate, over the reaction period, which provides for favorable reaction kinetics and which insures the before-mentioned 50 wt % concentration of HBr in the water. When aqueous HBr is used, it may be necessary to supplement its feed with gaseous HBr to replace the HBr which is used by the reaction, and thus lost from the water, so as to maintain the 50 wt % HBr concentration.

The catalyst used in the process may be a mono- or di-carboxylic acid, a mono- or di-carboxylic acid anhydride, a mono or di-carboxylic acid ester or a mixture of two or more of such catalysts. The catalyst may also be a halogenated derivative of such acids, anhydrides, and esters. Exemplary of useful catalysts are, acetic acid, adipic acid, propionic acid, hexanoic acid, butyric acid, chloroacetic acid, benzoic acid, succinic acid, caprylic acid, glutaric acid, lauric acid, phthalic anhydride, acetic anhydride, acetates of DBNPG, and the like. Preferred catalysts are those aliphatic mono- or di-carboxylic acids which contain from 2 to about 8 carbon atoms. Their anhydrides and esters are likewise preferred. Most highly preferred are acetic acid, adipic acid and acetates of DBNPG.

The amount of catalyst used in the process is generally from about 0.1 to about 10 mol % of catalyst based upon the amount of pentaerythritol charged to the reactor. It is preferred that from about 0.5 to about 3 mol % catalyst be used.

Selection of the substantially inert solvent is based upon the solvent's ability to act as a reaction solvent and be a good solvent for tribromoneopentyl alcohol but not for DBNPG at the temperature of the reaction mass when the DBNPG is precipitated therefrom. Suitable solvents can be selected from aromatic hydrocarbons, cycloaliphatic hydrocarbons, and halogenated aliphatic hydrocarbons. Mixtures of solvents also can be used. Exemplary solvents are toluene, benzene, cyclohexane, perchloroethylene, trichloroethylene, chlorobenzene, dichlorobenzene, methylenedibromide, dibromoethane, hexachlorocyclopentadiene, methylene chloride, ethylene dibromide, hexane, carbon tetrachloride, xylenes, and bromobenzene. The use of the lower boiling solvents may require running the process under pressure to prevent solvent loss from the reaction. The more preferred solvent is toluene. The amount of solvent used is not critical so long as the amount used provides for the two before-mentioned solvent functions.

The reaction temperature is that temperature which provides for bromination of the pentaerythritol. Temperatures, within the range of from about 80° C. to about 160° C. are suitable, with temperatures within the range of from about 100° C. to about 125° C. being most preferred as these preferred temperatures insure economical reaction times.

Necessarily, the reaction will be run at a pressure which will prevent substantial loss of water, solvent and HBr from the reactor at the reaction temperature. From the standpoint of obviating the need for high pressure reactors, the use of pressures from about 0 psig to about 150 psig are preferred. The lower end of the pressure range would be used with the lower reaction temperatures while higher pressures would be used with the higher reaction temperatures.

The reaction time is that amount of time needed to obtain the best yields of DBNPG for the particular reaction variables selected. When using the preferred mole ratios, temperatures, catalysts, etc. described above, the reaction time will usually be less than about 5 hours.

The presence of water in the reaction mass is useful as it acts to solubilize and hold in solution (1) a major portion of the monobromopentaerythritol and (2) any water-soluble neutralization products formed during the neutralization step. After the reaction time has lapsed, additional water can be added to the reaction mass to provide sufficient water for these purposes. However, such addition is not necessary if the amount of by-product water present in the reaction mass is sufficient. Since it is more convenient to add extra water to the reaction mass than it is to determine if the maximum amount of monobromopentaerythritol and water-soluble neutralization products have been dissolved, this addition is preferred. If water is to be added, the amount of water should be from about 0.5 L to about 2 L of water per L of reaction mass.

Neutralization of the reaction mass is easily accomplished by adding a basic compound or an acid scavenger to the reaction mass. The basic compounds can be, for example, $NaHCO_3$, $K_2CO_3$, $Na_2CO_3$, $KHCO_3$, $Ca(OH)_2$, CaO, MgO, and the like. Preferred basic compounds are the basic alkali metal and alkaline earth metal salts as they readily and efficiently form water-soluble bromide salts. U.S. Pat. No. 3,876,509 discloses various oxiranes and oxetanes which are suitable acid scavengers. It is preferred that the basic compound or scavenger, which is chosen for neutralization, yield a neutralization product which is soluble in either or both of the solvent and water present in the reaction mass at neutralization. The amount of basic compound or acid scavenger used is that amount which at least will effectively neutralize the HBr still present in the reaction mass.

It is preferred that the reaction mass be stirred during the reaction and neutralization steps of the process to insure good reagent contact and to insure that the solvent and water make maximum contact with the monobromopentaerythritol, tribromoneopentyl alcohol, and neutralization products.

After neutralization the reaction mass is cooled sufficiently to effect precipitation of DBNPG therefrom while avoiding any substantial precipitation of monobromopentaerythritol, tribromoneopentyl alcohol and neutralization products. To these ends a suitable cooling will be achieved by bringing the reaction mass to a temperature within the range of from about 10° C. to about 30° C. The precipitate will be a product highly predominant in DBNPG.

The precipitate is recovered from the reaction mass by any method which does not cause precipitation of any significant amounts of monobromopentaerythritol, tribromoneopentyl alcohol, and neutralization products. A preferred recovery technique is conventional filtration or centrifugation.

After the precipitate is recovered, it can be washed with cold water (15° C. or below) and with cold toluene (15° C. or below). After washing, if it is done, the precipitate is conventionally dried.

The dried precipitate is a product which is highly pure in DBNPG. Indeed, products containing over 95 wt % DBNPG have been obtained by the practice of this invention. Products containing 99+ wt % are possible and have also been obtained.

Pentaerythritol is also known as 2,2-bis(hydroxymethyl)-1,3-propanediol. The monobromopentaerythritol, the DBNPG and the tribromoneopentyl alcohol can also be referred to as, respectively, 2-(bromomethyl)-2-(hydroxymethyl)-1,3-propanediol, 2,2-bis(bromomethyl)-1,3-propanediol, and 3-bromo-2,2-bis(bromomethyl)-1-propanol.

EXAMPLE I

To a 6-oz Fisher-Porter tube was added 13.6 g of pentaerythritol (0.1 mol), 30 g toluene and 0.292 g adipic acid (0.002 mol). The tube was fitted with a magnetic stirrer which was used to keep the reaction mass mixed. The resultant reaction mass was heated to about 125° C. Gaseous HBr was fed to the tube over a period of 2 hrs. The total HBr feed amounted to 24.3 g (0.3 mol). After the HBr feed, the reaction mass was maintained at about 125° C. for an additional hour. After the reaction time of 3 hrs had elapsed, 30 mL of $H_2O$ was added at 80° C. and the reaction mass temperature dropped to 40° C. Then 7.25 g of $NaHCO_3$ and 0.5 g $K_2CO_3$ were added for neutralization purposes. The reaction mass was then heated to 50° C. for 15 min and then cooled to 10° C. to form a precipitate. The precipitate was filtered from the reaction mass. The precipitate was washed with 30 mL cold water and 15 mL cold toluene. The washed solids were then air dried to yield a white product. This product was determined by gas chromatography to be 99.3% pure DBNPG. The product weighed 18.9 g, representing a 72% yield based upon starting pentaerythritol. The filtrate separated into two layers, a toluene layer and a water layer. The toluene layer was found by gas chromatography to contain 0.001 mol of DBNPG and 0.013 mol of tribromoneopentyl alcohol. The water layer contained 0.006 mol each of monobromopentaerythritol and DBNPG.

What is claimed:

1. A process for preparing dibromoneopentyl glycol, which process comprises:
   (a) brominating pentaerythritol with HBr to yield a reaction mass containing dibromoneopentyl glycol and lesser amounts of monobromopentaerythritol and tribromoneopentyl alcohol, said bromination occurring in the presence of a catalyst selected from the group consisting of mono- or di-carboxylic acids, their anhydrides, their esters, and mixtures thereof, and in the presence of a substantially inert solvent, which solvent has, at the temperature to which the reaction mass is cooled in (d), a solubility for said tribromoneopentyl alcohol greater than that for said dibromoneopentyl glycol;
   (b) maintaining in the reaction mass at least a major portion of the by-product water formed by the bromination in (a);
   (c) neutralizing the reaction mass;
   (d) cooling said reaction mass sufficiently to form a precipitate which is predominant in said dibromoneopentyl glycol; and
   (e) recovering said precipitate from the reaction mass.

2. The process of claim 1 wherein said solvent is selected from the group consisting of toluene, xylene, benzene, or perchloroethylene.

3. The process of claim 1 wherein said neutralization is effected by the addition of a basic alkali metal salt or alkaline earth metal salt to the reaction mass.

4. The process of claim 3 wherein said basic metal salt is $NaHCO_3$, $K_2CO_3$, $Na_2CO_3$, $KHCO_3$, $Ca(OH)_2$, CaO, MgO, or mixtures thereof.

5. The process of claim 1 wherein prior to (c) water is added to said reaction mass.

6. The process of claim 1 wherein said recovery of said precipitate from said reaction mass is effected by filtration or by centrifugation.

7. The process of claim 1 wherein said bromination occurs at a temperature within the range of from about 80° C. to about 160° C.

8. The process of claim 1 wherein the molar ratio of said pentaerythritol to said HBr is within the range of from 1:2.5 to about 1:3.

9. The process of claim 1 wherein the reaction mass is cooled in (d) to a temperature within the range of from about 10° C. to about 30° C.

10. The process of claim 1 wherein said catalyst is adipic acid, acetic acid, or mixtures thereof.

* * * * *